(12) United States Patent
Edgson et al.

(10) Patent No.: US 6,426,629 B1
(45) Date of Patent: Jul. 30, 2002

(54) METHOD AND APPARATUS FOR MEASURING AN ELECTRICAL PARAMETER OF A FLUID

(75) Inventors: Raymond Edgson, Hertfordshire; Eric Wilkinson, Cambridgeshire, both of (GB)

(73) Assignee: Gambro AB (SE)

( * ) Notice: Subject to any disclaimer, the term of this patent is extended or adjusted under 35 U.S.C. 154(b) by 0 days.

(21) Appl. No.: 09/101,543

(22) PCT Filed: Jan. 13, 1997

(86) PCT No.: PCT/GB97/00098

§ 371 (c)(1),
(2), (4) Date: Jul. 10, 1998

(87) PCT Pub. No.: WO97/25615

PCT Pub. Date: Jul. 17, 1997

(30) Foreign Application Priority Data

Jan. 11, 1996 (GB) .............................................. 9600541

(51) Int. Cl.[7] .......................... G01N 27/02; G01R 27/08
(52) U.S. Cl. ........................................ 324/439; 324/694
(58) Field of Search ................. 324/439, 441, 324/450, 73.61, 694, 698, 717

(56) References Cited

U.S. PATENT DOCUMENTS 2,422,873 A    6/1947   Wolfner
4,511,845 A    4/1985   Dauphinee et al.
5,140,275 A  * 8/1992   Schoerner et al. ....... 324/73.61
5,260,667 A  * 11/1993  Garcia-Golding et al. .. 324/694
5,644,239 A  * 7/1997   Huang et al. ............... 324/441

FOREIGN PATENT DOCUMENTS

| DE | 216397   | 11/1909 |
| DE | 1095007  | 12/1960 |
| DE | 3900119  | 8/1990  |
| NL | 8300782  | 10/1984 |
| WO | 96/04401 | 2/1996  |

* cited by examiner

Primary Examiner—N. Le
Assistant Examiner—James Kerveros
(74) Attorney, Agent, or Firm—Lerner, David, Littenberg, Krumholz & Mentlik, LLP

(57) ABSTRACT

Methods and apparatus for measuring electrical parameters of a test fluid are disclosed. The methods include maintaining the test fluid and a reference fluid at the same temperature and in thermal proximity to each other, equalizing the temperature of the test fluid and the reference fluid prior to the measuring step, measuring the electrical parameter of the test fluid and the reference fluid at substantially the same time, and standardizing the measurement to a predetermined temperature. The apparatus includes a heat exchanger for maintaining the flow of a primary heat exchange fluid in thermal proximity to the test fluid in the reference fluid, and a metal wall having one surface in contact with a measuring cell and another surface in contact with the flow of the primary heat exchange fluid whereby the measuring cell and the heat exchanger are separated thereby.

38 Claims, 3 Drawing Sheets

METHOD AND APPARATUS FOR MEASURING AN ELECTRICAL PARAMETER OF A FLUID

FIELD OF THE INVENTION

The present invention relates to a method of measuring an electrical parameter of a fluid. In particular the present invention concerns the measurement of the electrical conductivity of fluid.

BACKGROUND OF THE INVENTION

Electrical conductivity is a property of a fluid which may be used in the identification of fluids and in the measurement of the concentration of certain constituents of a solution or mixture of different materials, including bubbles and solids in a fluid medium. The principle of such concentration measurement is that the constituents have a different electrical conductivity as compared to that of the base material, such that the electrical conductivity of the combination varies with the concentration.

Electrical conductivity is measured by passing an electrical current through the fluid and calculating the electrical resistance from the voltage drop across the fluid divided by the current. This is done in a device called a conductivity cell, which contains at least two electrodes separated by the fluid to be measured. The electrical current enters and leaves the fluid by means of electrodes, which are normally arranged so that they are electrically insulated from one another apart from the fluid path.

The electrical conductance is calculated as the inverse of the electrical resistance. Thus, electrical conductance depends not only on the electrical conductivity, but also on the geometry of the electrical path through the fluid and any additional electrical paths (which are normally minimized). In many situations, the conductance C is related to the conductivity P by a simple constant k (which is usually termed the cell constant) as shown in equation 1.

$$\rho = kc \qquad 1$$

This relationship follows from simple electrical theory, which states that the conductance equals the conductivity times the conductor cross-sectional area divided by the conductor length. In other words, the cell constant equals the conductor length divided by the conductor cross sectional area. Conventionally, the cell constant is established by calibrating the conductivity cell with fluid of known conductivity—typically potassium chloride.

To prevent polarization of the electrodes, whereby an excess (or deficit) of charge builds up at and around the point at which the electrical signal enters and leaves the fluid, alternating current is conventionally used instead of direct current.

Conductivity cells may be arranged to accept a flowing fluid or to measure a static pool of fluid according to the nature of the application.

The conductivity of a fluid depends on temperature and a change of about 2% per degree centigrade is fairly typical. Therefore, in many conductivity measuring devices, a temperature probe is used to measure the temperature, so that a correction may be made for any difference between the actual measurement temperature and the reference temperature (which is often 25° C.).

However, accurate temperature compensation is difficult for a number of reasons. The first of these is that the point and time at which the temperature is measured is not (in general) the same point and time at which the conductivity is measured. Thus, any change in the temperature between the temperature measurement and the conductivity measurement results in an error. This problem is exacerbated by the fact that both the temperature measurement and the conductivity measurement usually generate heat as a by product of the measurement technique. At low flow rates, these heating effects have a greater affect on the temperature of the fluid and, at the same time, the temperature probe must be better isolated from the environment to ensure that is neither added nor removed from the fluid by the temperature probe. The lower the flow rate, however, the greater the errors introduced by these problems such that the accuracy which can be obtained with known techniques reduces as the flow rate reduces.

These problems also affect the calibration of the cell when the temperature must also be determined very accurately. This means that the errors are encountered twice in the total measurement process, rather than just at the time of the conductivity measurement of the test fluid. In addition, if the variation of the conductivity with temperature is not accurately known for both the calibration fluid and the test fluid, further errors may be generated in the temperature correction process.

An additional problem with conductivity cells is that the cell constant may change with time and regular re-calibration is required if accurate performance is to be maintained.

PCT Application No. WO-A-9 604 401 discloses methods and apparatus for measuring the differential conductivity of decomposed and undecomposed urea solutions. The present invention is also applicable to such application, and the entire disclosure of WO-A-9 604 401 is incorporated herein by reference thereto.

SUMMARY OF THE INVENTION

In accordance with the present invention, these and other objects have now been accomplished by the discovery of a method for measuring an electrical parameter of a test fluid comprising maintaining the test fluid and a reference fluid at substantially the same temperature and in thermal proximity to each other, equalizing the temperature of the test fluid and a reference fluid prior to the measuring step, measuring the electrical parameter of the test fluid and the reference fluid at substantially the same time, and standardizing the measurement to a predetermined temperature. Preferably, measuring of the electrical parameters is carried out in the measurement cell. In a preferred embodiment, the standardizing of the measurement to the predetermined temperature is carried out on the basis of the relationship:

$$\rho_b(\theta) = \rho_b \rho_a(\theta) - \rho_a)$$

wherein θ comprises a standard temperature, $\rho_b(\theta)$ comprises the electrical parameter of the test fluid at the standard temperature, $\rho_a(\theta)$ comprises the electrical parameter of the reference fluid at the standard temperature, $\rho_b$ comprises the electrical parameter of the test fluid at the measured temperature, and $\rho_a$ comprises the electrical parameter of the reference fluid at the measured temperature.

In accordance with one embodiment of the method of the present invention, the reference fluid comprises a calibration fluid.

In accordance with another embodiment of the method of the present invention, the reference fluid is provided by subjecting the test fluid to a predetermined process wherein the electrical parameter is altered. In a preferred embodiment, measuring of the electrical parameter comprises comparing the electrical parameter of a test fluid to the electrical parameter of the reference fluid.

In accordance with a preferred embodiment of the method of the present invention, standardizing of the measurement to the predetermined temperature is determined on the basis of the relationship:

$$\rho_b(\theta) - \rho_a(\theta) = \rho_b - \rho_a + 25(\alpha_b - \alpha_a) - T(\alpha_b - \alpha_a)$$

wherein T comprises the measurement temperature, $\alpha_b$ comprises the temperature coefficient of the electrical parameter of the test fluid, and $\alpha_a$ comprises the temperature coefficient of the electrical parameter of the reference fluid.

In accordance with another embodiment of the method of the present invention, the electrical parameter comprises conductivity. In accordance with another embodiment, the method includes disposing the measurement cell in thermal proximity to flowing primary heat exchange fluid. In a preferred embodiment, the measurement cell is thermally symmetrical about a plane wherein the test fluid and the reference fluid are symmetrically disposed about that plane.

In accordance with another embodiment of the method of the present invention, the method includes providing the primary exchange fluid to the measurement cell and withdrawing the primary heat exchange fluid from the measurement cell in that plane. In accordance with a preferred embodiment, the primary heat exchange fluid and the measurement cell are separated by a metal wall. Preferably, the measurement cell includes a measurement cell plate and the method includes flowing a portion of the primary heat exchange fluid through the metal wall to the measurement cell plate.

In accordance with another embodiment of the method of the present invention, the method includes isolating the measurement cell opposite a region of thermal proximity to the primary heat exchange fluid.

In accordance with another embodiment of the method of the present invention, the method includes flowing the test fluid and the reference fluid through flow paths during the measuring of the electrical parameter.

In accordance with another embodiment of the method of the present invention, the measurement cell comprises a material selected from the group consisting of aluminum and sapphire.

In accordance with another embodiment of the method of the present invention, equalizing of the temperatures of the test fluid and the reference fluid comprises flowing the test fluid and the reference fluid through separate coils of tubing in thermal contact with each other and with a primary heat exchange fluid.

In accordance with another embodiment of the method of the present invention, the method includes measuring at least three portions of the test fluid and the reference fluid.

In accordance with another embodiment of the method of the present invention, the measurement cell comprises a first measurement cell, and the method includes a second measurement cell in parallel with the first measurement cell.

In accordance with the apparatus of the present invention, apparatus is provided for measuring an electrical parameter of a test fluid comprising a measurement cell for receiving the test fluid and a reference fluid, a heat exchanger for maintaining the flow of a primary heat exchange fluid in thermal proximity to the test fluid and the reference fluid, and a metal wall having a first surface and a second surface, the first surface being in contact with the measuring cell and the second surface being in contact with the flow of the primary heat exchange fluid, whereby the measuring cell and the heat exchanger are separated thereby. Preferably, the heat exchanger includes a measuring plate for measuring the electrical parameter, the measuring plate having an exterior, and the heat exchanger maintains the flow of the primary heat exchange fluid over the exterior of the measurement plate.

In accordance with another embodiment of the apparatus of the present invention, the measurement cell is thermally symmetrical about a plane whereby the test fluid and the reference fluid are symmetrically disposed about that plane.

In accordance with another embodiment of the apparatus of the present invention, the measurement cell comprises a first measurement cell, and the apparatus includes a second measurement cell coupled to the heat exchanger.

In accordance with another embodiment of the apparatus of the present invention, the metal wall includes an aperture whereby the primary heat exchange fluid is in direct thermal contact with the measurement cell.

In accordance with another embodiment of the apparatus of the present invention, the apparatus includes a cover for isolating the measurement cell from environmental air.

According to one aspect of the present invention there is provided a method of measuring an electrical parameter of a test fluid comprising the steps of:

(a) providing measurement cell means for separately containing bodies of the test fluid and a reference fluid, the bodies being at substantially the same temperature and in thermal proximity to each other, (b) equalizing the temperatures of these fluids prior to introducing them into the measurement cell means, (c) measuring the electrical parameter of the body of test fluid and the body of reference fluid at substantially the same time, and (d) standardizing the measurement to a predetermined temperature on the basis of the relationship:

$$\rho_b(\theta) = \rho_b(\rho_a(\theta) - \rho_a).$$

where: $\rho_b(\theta)$ is the electrical parameter of the test fluid at a standard temperature $\theta$, $\rho_a(\theta)$ is the electrical parameter of the reference fluid at standard temperature $\theta$, $\rho_b$ is the electrical parameter of the test fluid at the measurement temperature, $\rho_a$ is the electrical parameter of the reference fluid at the measurement temperature, $\alpha_b$ is the temperature coefficient of the electrical parameter of the test fluid, and $\alpha_a$ is the temperature coefficient of the electrical parameter of the reference fluid.

When the temperatures of the test fluid and reference fluid are equalized prior to measurement, temperature related errors in the measurement can be reduced.

In one embodiment of the method of the present invention, the reference fluid has a known value of the parameter and is used as a calibration fluid to calibrate the measurement of the electrical property of the test fluid.

In another embodiment of the method of the present invention, a differential measurement is made and it is not necessary for the parameter of the reference fluid to be known.

Preferably, the method of the present invention further comprises placing the test fluid and the reference fluid in separate cells which are in thermal contact and more preferably comprises a further step of passing the test fluid and reference fluid through a pair of secondary coils in a heat exchanger to ensure thermal equilibrium of the fluids. The reference fluid preferably undergoes a modification step which alters the electrical property of the reference fluid, and preferably the reference fluid is the same as the test fluid.

In another aspect, the present invention provides apparatus for determining an electrical parameter of a test fluid in relation to that of a reference fluid, comprising test cell means arranged to receive a body of the test fluid and a body of the reference fluid and heat exchange means for generating a flow of primary heat exchange fluid in thermal proximity to the bodies of test fluid and reference fluid, the heat exchange means comprising a metal wall having one surface in contact with the measurement cell means and an opposite surface in contact with the flow of primary heat exchange fluid, whereby the measurement cell means is outside the heat exchange means.

Rather than attempting to measure the temperatures of the calibration fluid and the test fluid accurately, the electrical conductivities of the two fluids are preferably measured at essentially the same time as each other using a pair of cells which are in close thermal proximity to one another, such that a substantial temperature difference cannot exist between them. Most of the temperature related errors then cancel out and there is no heating generated by the temperature measurement.

Preferably the measurement cell means is thermally symmetrical about a plane midway between the bodies of test fluid and reference fluid, the bodies being symmetrically disposed about the plane.

To ensure that the temperatures of the two fluids are the same as each other as they enter their respective cells, they may optionally be passed through a pair of secondary coils of a heat exchanger, which is preferably also used to control the temperature of the cells. The temperature of the fluid in the cells can be measured indirectly by measuring the temperature of the fluid in the primary flow path of the heat exchanger. The flow rate through the primary path can generally be higher because the primary fluid can be recirculated, whereas the test fluid is often only available in limited quantities. This means that the temperature can be measured more readily without the limitations described above.

As noted above, two preferred modes of operation are possible, namely one in which the reference fluid is a calibration fluid, whose electrical conductivity has been characterized under exacting conditions, with ample quantities and time for each measurement, and a second in which a differential measurement is made. This differential mode is particularly relevant when a fluid can be split into two paths, with the conductivity of one path being modified by some process before the conductivities of both paths are compared. In this case, the important factor is the change caused by processing one path (rather than the absolute value of the conductivity).

In the first case, the temperature need not be measured (directly or indirectly) as shown by the following analysis:

The electrical conductivity of cell a can be represented by the following equation:

$$\rho_a = \rho_{a25} + \alpha_a(T_a - 25) \qquad 2$$

where $\rho_a$=measured electrical conductivity in cell a $T_a$=temperature in cell $\rho_{a25}$=electrical conductivity of fluid in cell a at 25° C.

$\alpha_a$=rate of change of electrical conductivity with temperature

This is the equation used with single cell conventional measurements and it will be appreciated that an error in the temperature measurement leads directly to an error in the conductivity.

For twin cell measurement, a similar equation can be written for the second cell, as follows:

$$\rho_b = \rho_{b25} + \alpha_b(T_b - 25) \qquad 3$$

where $\rho_b$=measured electrical conductivity in cell b $T_b$=temperature in cell $\rho_{b25}$=electrical conductivity of fluid in cell b at 25° C.

$\alpha_b$=rate of change of electrical conductivity with temperature

Provided the temperatures $T_a$ and $T_b$ are equal, these two equations can be combined to provide an expression for the conductivity of the fluid in cell b in terms of the two cell measurements and the known properties, but without knowledge of the temperature. Thus, the conductivity of the fluid in cell b referred to 25° C. is:

$$\rho_{b25} = \rho_b + (\rho_{a25} - \rho_a)\,\alpha_b/\alpha_a \qquad 4$$

For the second mode of operation, the differential referred to 25° C. ($\rho_{b25} - \rho_{a25}$) can be found, again provided $T_a = T_b$, as follows:

$$\rho_{b25} - \rho_{a25} = \rho_b - \rho_a + 25(\alpha_b - \alpha_a) - T(\alpha_b - \alpha_a) \qquad 5$$

Although this is not completely independent of temperature, the accuracy with which the temperature must be known is less than for a single cell device, because $\alpha_b$ and $\alpha_a$ are normally equal or very close to each other. This means that the indirect temperature measurement technique described above is particularly suitable.

A similar analysis is applicable to the measurement of other electrical parameters, for example capacitance or dielectric loss tangent.

The use of two cells in the same device also allows for re-zeroing of the two cells against each other. This means that changes in the cell constant can be detected and a compensation made without the need for a re-calibration.

As previously mentioned, the two cells are preferably in close thermal proximity to each other and this is best achieved by making them from a material with a high thermal conductivity, but low electrical conductivity, to ensure that the electrodes are insulated from each other (except for the path through the fluid). Particularly suitable materials are alumina ceramic and sapphire or metals with an insulating coating such as glass. Close thermal proximity can also be enhanced by making the distance between the flows paths of the cells small and by making the entire construction symmetrical with respect to heat flows, so that there is no significant heat flow from one cell to the other (which would cause a temperature difference). Furthermore, the entire cell assembly should preferably be placed in close thermal proximity to the primary side of the heat exchanger by attaching the cells to a thermally conductive wall of the heat exchanger.

It will be understood that the measurement of the conductance of the electrical path through the fluid in the cell is achieved by conventional means and as such is not described in detail.

BRIEF DESCRIPTION OF THE DRAWINGS

A preferred embodiment of the present invention will now be described purely by way of example, with reference to the accompanying drawings in which.

DETAILED DESCRIPTION

Figure 1:
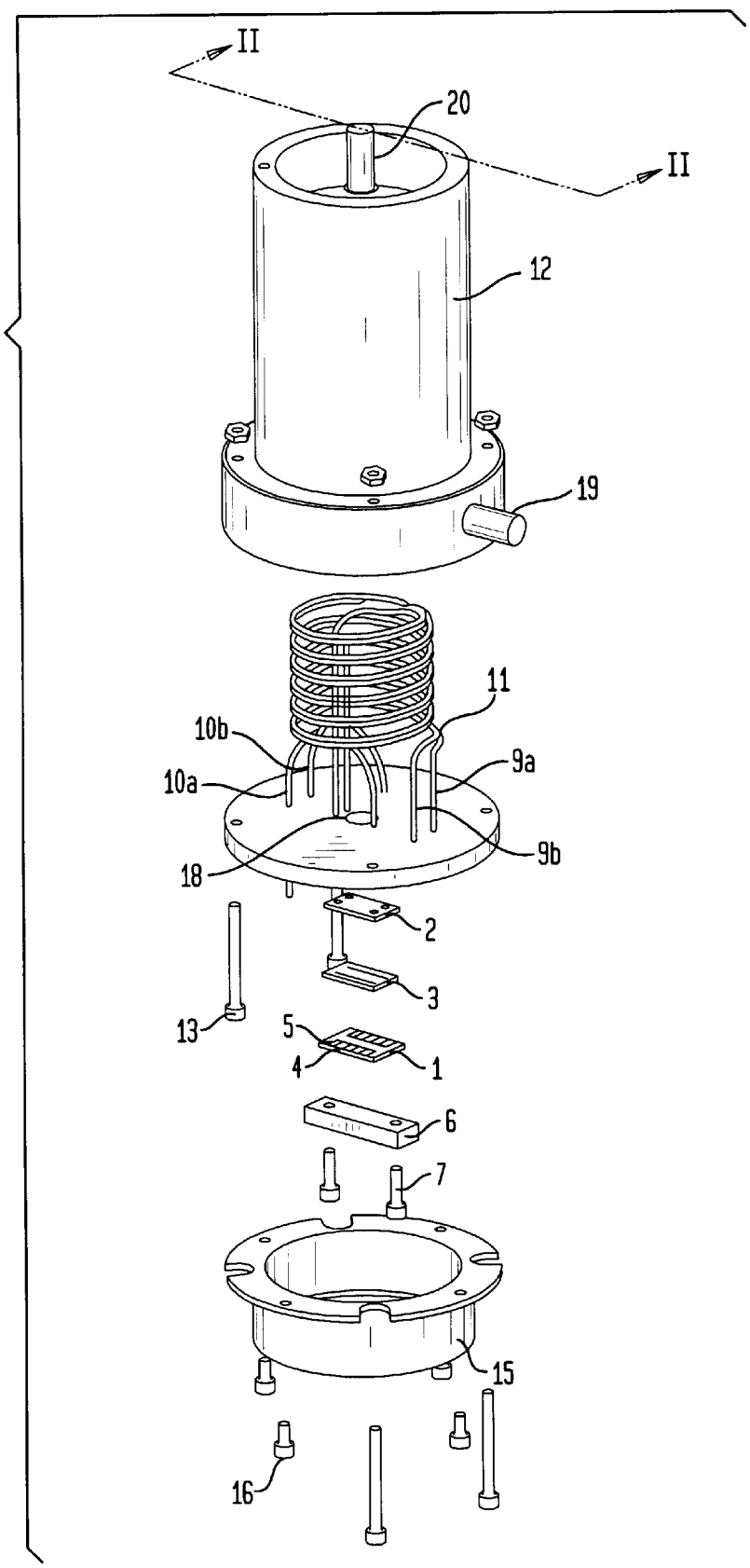
FIG. 1 is an exploded, perspective view of a cell and heat exchanger in accordance with the present invention.

The embodiment shown in FIGS. 1 to 4 is considered first from the point of view of the test fluids, which enter the secondary side of the heat exchanger through tubes 9a and 9b. These tubes are long enough to ensure that the two test fluids reach the same temperature as the primary heat exchanger fluid and each other within close limits. The tubes are made from a thermally conductive material such as steel, as this minimizes the length of tube required in order for the temperatures to stabilize. The tubes 9a and 9b are coiled together so that they are in close thermal proximity. This minimizes the possibility of a temperature difference being established between them.

From the heat exchanger, these tubes pass directly into cell top plate 2, which has holes to locate the tubes, which must be sealed with adhesive or other suitable means. After passing through these holes, the fluids enter flow channels in intermediate plate 3 such that they pass in flow paths 17 (FIGS. 3 and 4) over the electrodes on bottom plate 1. The fluids then flow back through the top plate and into exit tubes 10a and 10b, which may pass directly to the outside or else first pass through the heat exchanger if that is more convenient. The exit tubes 10a and 10b are also sealed with respect to the cell top plate 2. Further seals are employed where the tubes 9a, 9b, 10a and 10b pass through bulkhead plate 8, so as to prevent leakage of the primary heat exchanger fluid.

A clamp plate 6 and screws 7 retain the bottom plate 1, the intermediate plate 3 and the top plate 2 to the bulkhead 8 with the aid of tapped holes in the bulkhead. Additionally, non-electrically conductive sealants such as epoxy adhesives may be employed to ensure a seal between each of these components and also to ensure that no fluid passes from one flow path to the other. The sealant layer is best kept as thin as possible to ensure that all of these cell components remain as closely as possible at the same temperature.

Figure 2:
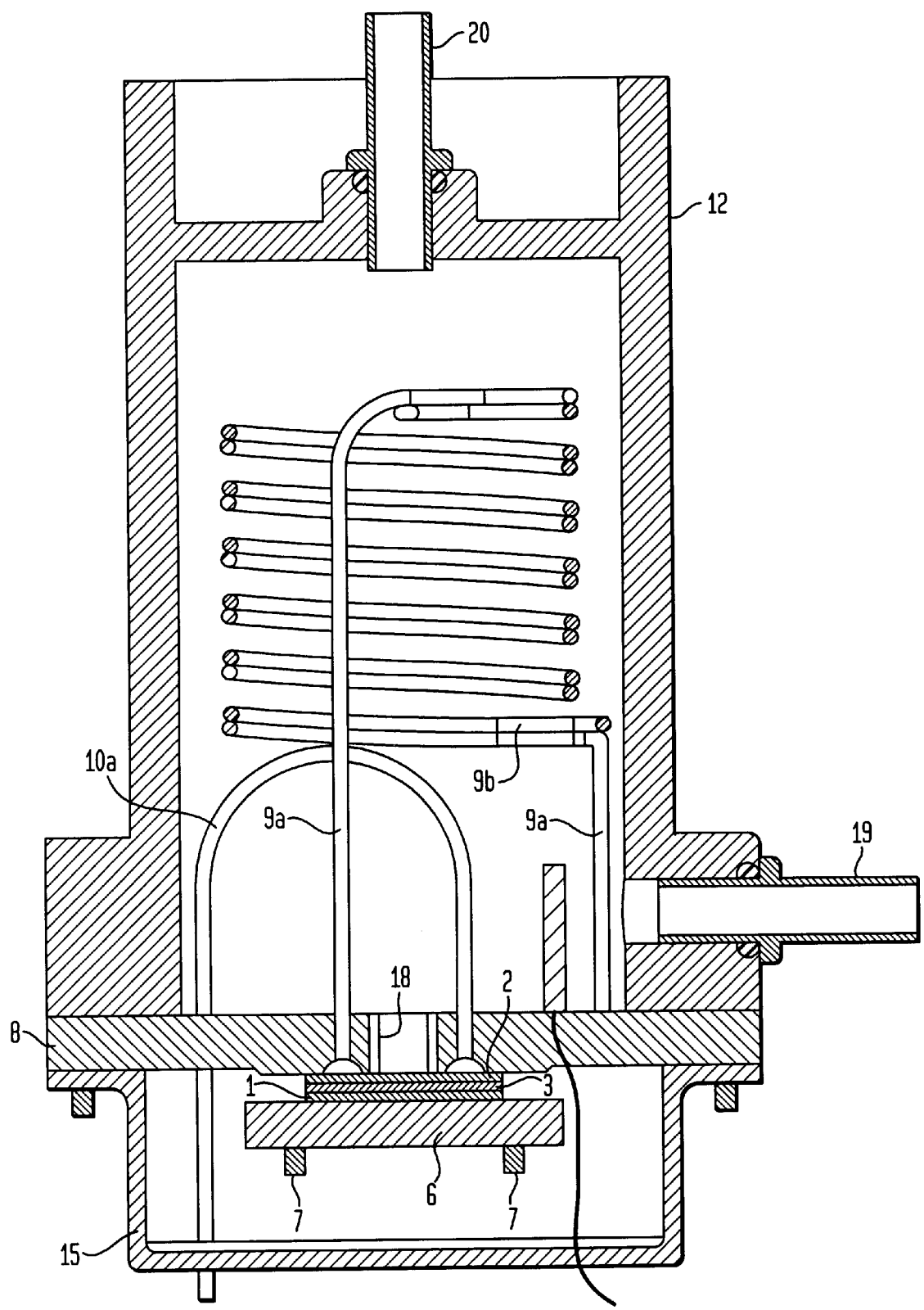
FIG. 2 is a front, elevational, cross-sectional view of the cell and heat exchanger taken along lines II—II of FIG. 1.
Figure 4:
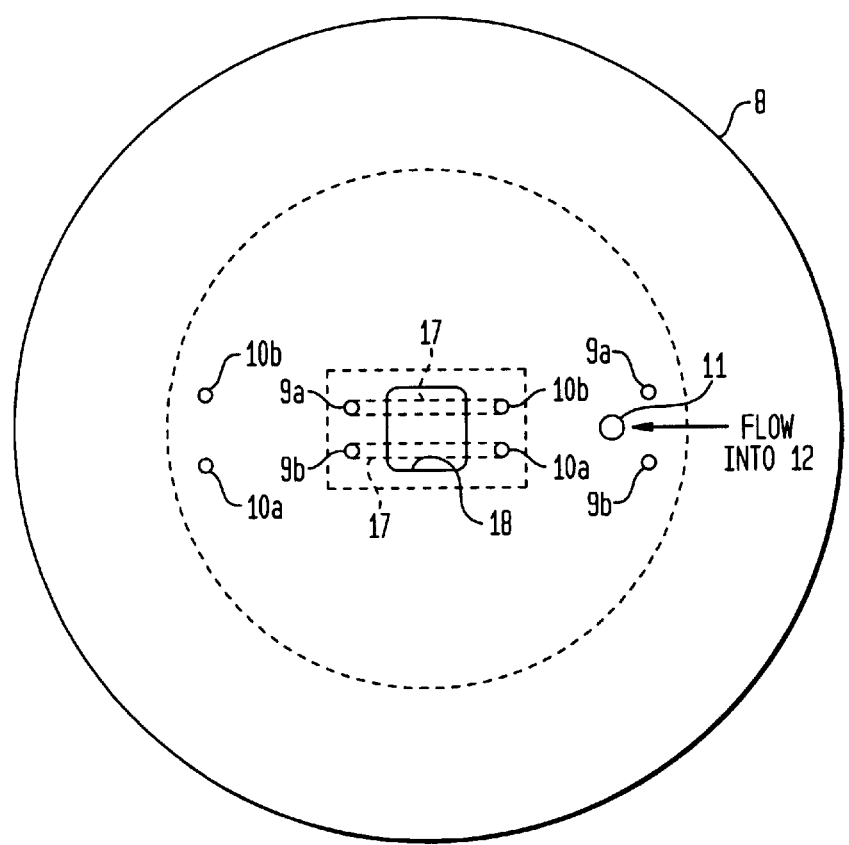
FIG. 4 is a top, elevational, plan view of plate 8 shown in FIG. 1.

A cut-out 18 is provided in the bulkhead 8, as shown in FIGS. 2 and 4, so as to allow the primary heat exchanger fluid to be in direct thermal contact with the cell top plate 2. The bulkhead is preferably made from a thermally conductive material such as steel or another suitable metal, and is preferably as thin as possible to ensure a close thermal contact consistent with the need to maintain a seal against the top plate 2. A temperature probe 11 such as a platinum resistance thermometer may be placed in the bulkhead 8 to measure the primary fluid temperature.

The primary heat exchanger fluid is within a cover 12, retained to the bulkhead by screws 13 and nuts 14 and a seal such as a gasket (not shown). The cover 12 may be conveniently manufactured from a polymer material such as polypropylene. An inlet 19 and outlet 20 are provided in the plane of FIG. 2 within the cover 12 to allow the primary fluid to enter and leave the primary circuit, passing over the coils 9a and 9b in the process. These connections are preferably arranged so that the primary fluid enters and leaves in the plane of FIG. 2, which lies centrally between the two flow channels in the intermediate plate 3 and perpendicular to the plane of the bulkhead 8. The whole arrangement is designed to minimize thermal asymmetries about this plane.

An additional cover 15, which is retained by screws 16, is designed to isolate the cell components 1, 2 and 3 from the environmental air, so as to maintain the cell and the primary fluid at a similar temperature and also to maintain the thermal symmetry about the plane described above. To ensure that the air around the cell components is kept close to the temperature of the heat exchanger, the primary fluid can be routed through the cover 15 or the space between the cover and the clamp plate 6 or even through the clamp plate 6. This is, however, a refinement which has not normally been found to be necessary.

The cell bottom plate provides a substrate for electrodes 4, which may be of vacuum deposited gold or platinum or other materials known in the art. Lead wires 5 carry the electrical signals to and from the electrodes. The electrode configuration may be any of those known in the art including the simplest two electrode (per flow channel) arrangement which is not ideally suited to high accuracy measurement. A conventional four electrode measurement, with the outer electrode pair being used to deliver the power and the inner part being used for sensing, is a particularly suitable configuration.

Figure 3:
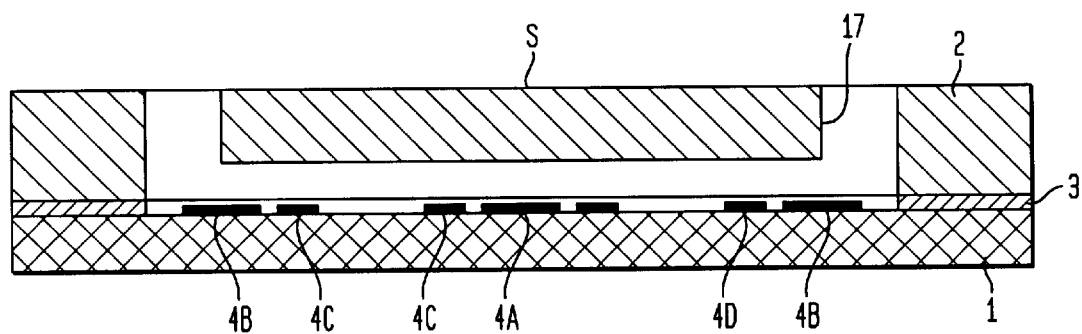
FIG. 3 is a side, elevational, cross-sectional view of one measurement cell taken parallel to lines II—II of FIG. 1.

In the embodiment as shown in FIG. 3, a seven electrode arrangement is shown, comprising a central electrode 4A of one polarity and two outer electrodes 4B of opposite polarity to electrode 4A. The resistance is determined by measuring the current between inner electrode 4A and outermost electrodes 4B, and by measuring the voltage i) between electrodes 4C and ii) between electrodes 4D in the standard manner.

The cell components 1, 2 and 3 are best manufactured from a material such as alumina or sapphire, which is electrically insulating but thermally conductive. Ocher cheaper materials including polymers and glasses may be employed, but the performance is not quite as good.

The device described above was designed for the following operating conditions and has certain key dimensions as listed:

| | |
|---|---|
| Conductivity range: | 0 to 50 mS/cm (at 25° C.) |
| Accuracy: | 5 $\mu$S/cm |
| Primary Flow Rate: | 500 ml/min |
| Secondary Flow Rate: | 1 ml/min (per channel) |
| Max Difference Between Inlet Temperatures: | 10° C. |
| Nominal Cell Constant: | 50 cm$^{-1}$ |
| Cell Channel Width: | 1 mm |
| Cell Channel Height: | 0.5 mm |
| Cell Gauge Length: | 2.5 mm |
| Secondary Tube Length: | 800 mm |
| Secondary Tube Bore: | 1 mm |
| Secondary Tube Diameter: | 1.6 mm |

The invention is particularly suitable for use in analytical instruments for measuring the concentration of a particular substance in a fluid. Potentially any substance which can be converted (such as by a chemical reaction) into another substance which has a different electrical conductivity is suitable for such a device. A further application is as a straight forward conductivity meter for fluids in laboratory or industrial processes. Another application is a reference meter for the calibration of other conventional cells.

It will be understood that the present invention has been described purely by way of example, and that modifications of detail can be made within the scope of the invention. For example, two or more measurement cells in parallel could be thermally coupled to a common heat exchanger.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of measuring an electrical parameter of a test fluid comprising equalizing the temperature of said test fluid and a reference fluid by maintaining said test fluid and said reference fluid in thermal proximity to each other to equalize the temperature of said test fluid and said reference fluid prior to said measuring, substantially maintaining said equalized temperatures, measuring said electrical parameter of said test fluid and said reference fluid at the same time, and at the point on their respective flow paths while said temperatures of said test fluid and said reference fluid remain equalized and standardizing said measurement to a predetermined temperature.

2. The method of claim 1 wherein said measuring of said electrical parameter is carried out in a measurement cell.

3. The method of claim 2 wherein said measurement cell comprises a material selected from the group consisting of alumina ceramic and sapphire.

4. The method of claim 2 wherein said measurement cell comprises a first measurement cell, and including a second measurement cell in parallel with the first measurement cell.

5. The method of claim 2 including disposing said measurement cell in thermal proximity to flowing primary heat exchange fluid.

6. The method of claim 5 including isolating said measurement cell opposite a region of thermal proximity to said primary heat exchange fluid.

7. The method of claim 5 wherein said measurement cell is thermally symmetrical about a plane wherein said test fluid and said reference fluid are symmetrically disposed about said plane.

8. The method of claim 7 including providing said primary heat exchange fluid to said measurement cell and withdrawing said primary heat exchange fluid from said measurement cell in said plane.

9. The method of claim 7 wherein said primary heat exchange fluid and said measurement cell are separated by a metal wall.

10. The method of claim 9 wherein said measurement cell includes a measurement cell plate and including flowing a portion of said primary heat exchange fluid through said metal wall to said measurement cell plate.

11. The method of claim 1 wherein said standardizing of said measurement to said predetermined temperature is carried out on the basis of the relationship:

$$\rho_b(\theta)=\rho_b(\rho_a(\theta)-\rho_a)$$

wherein $\theta$ comprises a standard temperature, $\rho_b(\theta)$ comprises said electrical parameter of said fluid at said standard temperature, $\rho_b(\theta)$ comprises said electrical parameter of said reference fluid at said standard temperature, $\rho_b$ comprises said electrical parameter of said test fluid at said measured temperature, and $\rho_a$ comprises said electrical parameter of said reference fluid at said measured temperature.

12. The method of claim 1 wherein said reference fluid comprises a calibration fluid.

13. The method of claim 1 wherein said reference fluid is provided by subjecting said test fluid to a predetermined process wherein said electrical parameter is altered.

14. The method of claim 13 wherein said measuring of said electrical parameter comprises comparing said electrical parameter of said test fluid to said electrical parameter of said reference fluid.

15. Amended The method of claim 14 wherein said standardizing of said measurement to said predetermined temperature is determined on the basis of the relationship:

$$\rho_b(\theta)-\rho_a(\theta)=\rho_b-\rho_a+25(\alpha_b-\alpha_a)-T(\alpha_b-\alpha_a)$$

wherein T comprises said measurement temperature, $\alpha_b$ comprises the temperature coefficient of said electrical parameter of said test fluid, and $\alpha_a$ comprises said temperature coefficient of said electrical parameter of said reference fluid.

16. The method of claim 1 wherein said electrical parameter comprises conductivity.

17. The method of claim 1 including flowing said test fluid and said reference fluid through flow paths during said measuring of said electrical parameter.

18. The method of claim 1 wherein said equalizing of said temperatures of said test fluid and said reference fluid comprises flowing said test fluid and said reference fluid through separate coils of tubing in thermal contact with each other and with a primary heat exchange fluid.

19. The method of claim 1 comprising measuring at least three portions of said test fluid and said reference fluid.

20. The method of claim 1, wherein said standardizing of said measurement to said predetermined temperature is carried out on the basis of the relationship:

$$\rho_b(\theta)=\rho_b+(\rho_a(\theta)-\rho_a)^{\alpha_b/\alpha_a}$$

wherein $\theta$ comprises a standard temperature, $\rho_b(\theta)$ comprises said electrical parameter of said test fluid at said standard temperature, $\rho_a(\theta)$ comprises said electrical parameter of said reference fluid at said standard temperature, $\rho_b$ comprises said electrical parameter of said test fluid at said measured temperature, $\rho_a$ comprises said electrical parameter of said reference fluid at said measured temperature, $\alpha_b$ comprises the temperature coefficient of said electrical parameter of said test fluid, and $\alpha_a$ comprises said temperature coefficient of said electrical parameter of said reference fluid.

21. The method of claim 1, wherein said electrical parameter comprises a characteristic selected from the group of capacitance, dielectric loss tangent and concentration.

22. Apparatus for measuring an electrical parameter of a test fluid comprising a measurement cell for receiving said test fluid and a reference fluid, a heat exchanger for maintaining the flow of a primary heat exchange fluid in thermal proximity to said test fluid and said reference fluid, and a metal wall having a first surface and a second surface, said first surface being in contact with said measuring cell and said second surface being in contact with said flow of said primary heat exchange fluid, whereby said measuring cell and said heat exchanger are separated thereby.

23. The apparatus of claim 22 wherein said heat exchanger includes a measuring plate for measuring said electrical parameter, said measuring plate having an exterior, and wherein said heat exchanger maintains said flow of said primary heat exchange fluid over the exterior of said measurement plate.

24. The apparatus of claim 22 wherein said measurement cell is thermally symmetrical about a plane whereby said test fluid and said reference fluid are symmetrically disposed about said plane.

25. The apparatus of claim 22 wherein said measurement cell comprises a first measurement cell, and a second measurement cell each coupled to said heat exchanger.

26. The apparatus of claim 22 wherein said metal wall includes an aperture whereby said primary heat exchange fluid is in direct thermal contact with said measurement cell.

27. The apparatus of claim 22 including a cover for isolating said measurement cell from environmental air.

28. The apparatus of claim 22, wherein said reference fluid is a calibration fluid.

29. The apparatus of claim 22, wherein said measurement call comprises a material selected from the group consisting of alumina ceramic and sapphire.

30. The apparatus of claim 22, wherein said measurement cell comprises a first measurement cell and a second measurement cell in parallel with the first measurement cell.

31. An apparatus for determining an electrical parameter of a test fluid comprising a measuring cell means comprising a pair of cells each comprising a flow path for carrying a test fluid and a reference fluid respectively, each flow path comprising at least two electrodes, the cells being arranged in close thermal proximity.

32. The apparatus according to claim 31, comprising a heat exchanger for maintaining the flow of a primary heat exchange fluid in thermal proximity to said test fluid and reference fluid, and a metal wall having a first surface and a second surface, the first surface being in contact with said measuring cell means and the second surface being in contact with said flow of said primary heat exchange fluid, whereby said measuring cell means and said heat exchanger are separated thereby.

33. Apparatus according to claim 31, wherein said pair of cells are coupled to a heat exchanger.

34. The apparatus of claim 31, including a cover for isolating said measurement cell means from environmental air.

35. A method of determining an electrical parameter of a test fluid wherein the following steps are carried out:

providing a measuring cell means comprising a pair of cells each comprising a flow path for carrying a test fluid and a reference fluid respectively, each flow path comprising at least two electrodes;

providing a body of the respective fluid in the respective flow path in such a way that the electrodes are separated by the respective body of fluid;

equalizing temperatures of the respective fluids by maintaining them in close thermal proximity;

simultaneously conducting electrical measurements on the respective fluid;

determining the electrical parameter of the test fluid by standardizing the respective electrical measurement to a predetermined temperature on the basis of a predetermined relationship with the reference fluid.

36. The method according to claim 35 comprising:

conducting the electrical measurements by passing an electrical current between the at least two electrodes and across the respective body of fluid;

measuring simultaneously the voltage drop across the respective body of fluid; and determining the electrical parameter of the test fluid on the basis of the respective current and the respective voltage drop.

37. The method of claim 35, further comprising providing a flowing primary heat exchange fluid in thermal proximity to the respective flow paths.

38. The method of claim 35 wherein said equalizing of said temperatures of said test fluid and said reference fluid comprises flowing said test fluid and said reference fluid through separate coils of tubing in thermal contact with each other and with a primary heat exchange fluid.

* * * * *

UNITED STATES PATENT AND TRADEMARK OFFICE
CERTIFICATE OF CORRECTION

PATENT NO.    : 6,426,629 B1                                             Page 1 of 1
DATED         : July 30, 2002
INVENTOR(S)   : Raymond Anthony Edgson and Eric Wilkinson It is certified that error appears in the above-identified patent and that said Letters Patent is hereby corrected as shown below:

Column 1,
Line 41, "p=kc" should read -- p=kC --.

Column 2,
Line 7, "by product" should read -- by-product --.
Line 11, after "that" insert -- it --.

Column 9,
Line 58, after "said" insert -- test --.

Column 10,
Line 8, delete "Amended".

Column 11,
Line 16, delete "call" and insert therefor -- cell --.

Signed and Sealed this

Thirty-first Day of December, 2002

JAMES E. ROGAN
*Director of the United States Patent and Trademark Office*